(12) United States Patent
Park et al.

(10) Patent No.: US 8,552,189 B2
(45) Date of Patent: Oct. 8, 2013

(54) HYBRID POROUS MATERIAL AND METHODS OF PREPARING THE SAME

(75) Inventors: Kyo-sung Park, Seongnam-si (KR); Seon-ah Jin, Pocheon-si (KR); Hyun-chul Lee, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 365 days.

(21) Appl. No.: 12/853,460

(22) Filed: Aug. 10, 2010

(65) Prior Publication Data

US 2011/0144365 A1 Jun. 16, 2011

(30) Foreign Application Priority Data

Dec. 15, 2009 (KR) ........................ 10-2009-0125034

(51) Int. Cl.
*C07F 15/00* (2006.01)
*C07F 7/18* (2006.01)
*C07F 3/00* (2006.01)
*C07F 5/06* (2006.01)

(52) U.S. Cl.
USPC .......... 546/2; 548/101; 556/1; 556/9; 556/55; 556/106; 556/115; 556/132; 556/136; 556/150; 556/184

(58) Field of Classification Search
USPC .......... 556/1, 9, 55, 106, 115, 132, 136, 150, 556/184; 548/101; 546/2
See application file for complete search history.

(56) References Cited

U.S. PATENT DOCUMENTS

| 3,556,725 | A | 1/1971 | Chiola, et al. |
| 5,648,508 | A | 7/1997 | Yaghi |
| 6,211,104 | B1 * | 4/2001 | Shi et al. .................... 502/67 |
| 2011/0217217 | A1 * | 9/2011 | Bandosz et al. ............. 423/226 |

FOREIGN PATENT DOCUMENTS

| CN | 101348408 A | 1/2009 |
| CN | 101618337 A | 1/2010 |
| EP | 1287891 A2 | 3/2003 |
| FR | 2929278 A1 | 10/2009 |
| KR | 1999-018318 A | 3/1999 |
| KR | 1020090038638 A | 4/2009 |
| KR | 1020090090867 A | 8/2009 |
| WO | 2007091828 A1 | 8/2007 |

OTHER PUBLICATIONS

European Search Report for Application No. 10191963.7-2111 dated Feb. 2, 2011.
Rahul Banerjee, et al., "High-Throughput Synthesis of Zeolitic Imidazolate Frameworks and Application to CO2 capture", Sciencemag.org, 2008, vol. 319: 939-943.
M. Kadlecikova, et al., "The growth of carbon nanotubes on montmorillonite and zeolite (clinoptilolite)", ScienceDirect, 2008, 254: 5073-5079.
Roland A. et al., "Layer-by-Layer Liquid-Phase Epitaxy of Crystalline coordination Polymers at Surfaces", Angew. Chem. Int. Ed, 48, 2009, pp. 6205-6208.
H. M. Powell, "Structure of Clathrate Compounds", Nature, No. 4262, vol. 168, Jul. 7, 1951, pp. 11-14.

* cited by examiner

*Primary Examiner* — Porfirio Nazario Gonzalez
(74) *Attorney, Agent, or Firm* — Cantor Colburn LLP (57) ABSTRACT

A hybrid porous material including at least a first and a second porous material portion which are chemically bonded to each other and are each a different type of material.

12 Claims, 6 Drawing Sheets

HYBRID POROUS MATERIAL AND METHODS OF PREPARING THE SAME

CROSS-REFERENCE TO RELATED APPLICATIONS

This application claims priority to Korean Patent Application No. 10-2009-0125034, filed on Dec. 15, 2009, and all the benefits accruing therefrom under 35 U.S.C. §119, the content of which in its entirety is herein incorporated by reference.

BACKGROUND

1. Field

The present disclosure relates to a hybrid porous material and methods of preparing the same.

2. Description of the Related Art

Porous materials are used for separation of mixed gases, storage of gas, membranes, support for chemical reaction catalysts, and selective molecule absorption, including removal of offensive smells. Porous materials may also be used in pigment-supported organic solar cells, drug carriers, and low-k dielectric materials.

Examples of known porous materials include mesoporous silica, zeolite, metal oxides, porous clay, and activated carbon. However, these porous materials can have the following problems. First, their lifetime in use can be limited to several months due to their low adsorption capacities. Second, their adsorption capacities for basic gases, such as ammonia or an amine, can be low. Third, when surface-modification is performed to improve their adsorption selectivities, their adsorption capacities are often reduced and the ratio of modified surface area to total surface area is limited to a few percent.

To overcome these and other problems, metal-organic framework ("MOF") compounds, which are a newer type of porous material, have been developed. MOF compounds have a large surface area, for example up to 7,000 square meters per gram ($m^2/g$), a large adsorption capacity corresponding to the large surface area, and may have improved adsorption characteristics resulting from unrestricted surface modifications. However, the bonds between metals and organic materials of MOF compounds may be unstable in the presence of water, thus they may easily decompose in a humid environment. Therefore there remains a need for a porous material having improved stability in the presence of water, particularly if the materials also have improved adsorption capacity and/or improved adsorption specificity.

SUMMARY

Provided is a hybrid porous material including at least two different types of porous material portions that are chemically bonded to each other.

Provided is a method of preparing the hybrid porous material, including chemically bonding at least two different types of porous material portions.

Additional aspects will be set forth in part in the description which follows and, in part, will be apparent from the description.

According to an embodiment, a hybrid porous material includes at least a first porous material portion and a second porous material portion, which are chemically bonded to each other and are each a different type of material.

Each of the at least first and second porous material portions may include at least one porous material selected from the group consisting of a porous silica, a porous alumina, a porous carbon, a zeolite, an activated carbon, a porous metal oxide, a porous clay, an aerogel, a metal-organic framework ("MOF") compound, a zeolitic imidazolate framework ("ZIF") compound, and derivatives thereof.

Each of the MOF compound, the ZIF compound, and derivatives thereof may include at least one central metallic element selected from the group consisting of metallic elements of the Periodic Table, and an organic ligand.

The central metallic element may be at least one selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (Al), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb).

The organic ligand may include a functional group linkable to at least two metallic ions.

According to another aspect, the at least first and second material portions of the hybrid porous material includes the MOF and the mesoporous silica which are chemically bonded to each other.

According to another aspect, disclosed is a method of preparing a hybrid porous material. The method includes chemically bonding at least a first and second porous material, each of which are a different type of material, to form the hybrid porous material.

According to another aspect of the method, the method may include impregnating a second porous material with a metal precursor or organic ligand precursor for forming the first porous material, wherein the first porous material is different in material type from the second porous material; and reacting the impregnated second porous material with the organic ligand precursor or metal precursor for forming the first porous material.

The first porous material may include at least one material selected from the group consisting of the MOF compound, the ZIF compound, and derivatives thereof.

The second porous material may include at least one material selected from the group consisting of a porous silica, a porous alumina, a porous carbon, a zeolite, an activated carbon, a porous metal oxide, a porous clay, and an aerogel.

The metal precursor may include at least one metallic element selected from the group consisting of metallic elements of the Periodic Table.

The metal precursor may include at least one compound selected from the group consisting of a metal nitrate, a metal chloride, a metal bromide, a metal iodide, a metal acetate, a metal carbonate, a metal formate, a metal molybdate, a metal sulfate, a metal sulfide, a metal oxide, a metal fluoride, a metal phosphate, a metal perchlorate, a metal borate, and a metal hydroxide.

The organic ligand precursor may include an organic compound having a functional group linkable to at least two metallic ions.

The organic ligand precursor may include at least one organic compound selected from the group consisting of terephthalic acid, a substituted terephthalic acid, tribenzoic acid, imidazole, a substituted imidazole, pyridine, a substituted pyridine, pyrazole, a substituted pyrazole, tetrazole, and a substituted tetrazole.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs.

Figure 1:
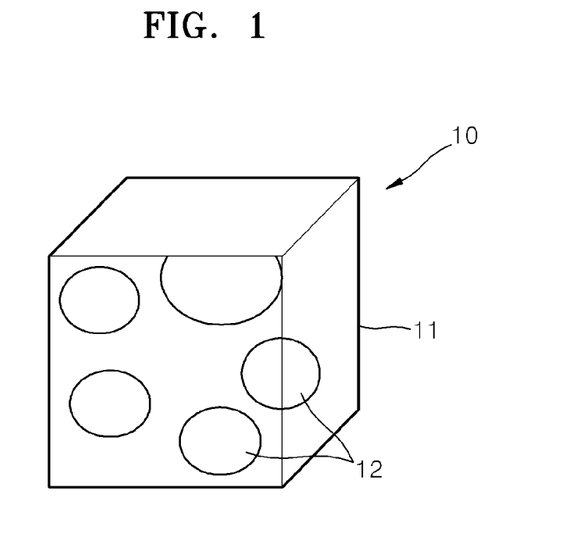
FIG. 1 is a schematic view of an exemplary embodiment of a hybrid porous material.

FIG. 1 is a schematic view of an exemplary embodiment of a hybrid porous material 10.

Referring to FIG. 1, the hybrid porous material 10 includes a first porous material portion 11 and a second porous material portion 12.

The first porous material portion 11 and the second porous material portion 12 may be chemically bonded and are different types of materials. In the present specification, the wording "different material types" and "different type of materials" means that each of the materials have different chemical compositions or different chemical structures.

Each of the first porous material portion 11 and the second porous material portion 12 may include at least one porous material selected from the group consisting of a porous silica, a porous alumina, a porous carbon, a zeolite, an activated carbon, a porous metal oxide, a porous clay, an aerogel, a metal-organic framework ("MOF") compound, a zeolitic imidazolate framework ("ZIF") compound, and a derivative thereof. For example, the first porous material portion 11 may include a MOF compound and/or a derivative thereof, and the second porous material portion 12 may include mesoporous silica and/or a derivative thereof.

A derivative of MOF compound may be prepared by dissolving 2-methylterephthalic acid and zinc nitrate tetrahydrate in diethylformamide (DEF), and heating the solution for a certain period of time (e.g. 100° C. for 12 hrs).

A derivative of ZIF compound may be prepared by dissolving imidazole and zinc nitrate tetrahydrate in dimethylformamide (DEF), and then heating the solution for a certain period of time (e.g. 140° C. for 24 hrs).

In the present specification, the term 'mesoporous silica' refers to porous silica having medium-sized pores, specifically, pores of about 2 nanometers (nm) to about 50 nm, more specifically 4 nm to about 40 nm, more specifically still about 25 nm.

In the present specification, the term "MOF compound" refers to a crystalline compound comprising metallic ions or metal clusters coordinated to often rigid organic molecules to form one-, two-, or three-dimensional structures that can be porous. In an embodiment, the MOF compound may consist of metallic ions or metal clusters and an organic ligand. In the present specification, the term "ZIF compound" refers to a nanoporous compound that comprises tetrahedral $MN_4$ clusters wherein M atoms are linked by an imidazolate ligand and wherein M is a metal. The ZIF compound may be used to substantially reduce or effectively prevent atmospheric emission of carbon dioxides because the ZIF compound has a capability of capturing carbon dioxide.

Each of the MOF compound, the ZIF compound, and derivatives thereof may include at least one central metallic element and an organic ligand. The central metallic element may be selected from the group consisting of transition metal elements and main group metal elements of the Periodic Table of the Elements. Alternatively, the central metallic element may be at least one selected from the group consisting a Group 3 to Group 16 element of the Periodic Table of the Elements, according to the group classification system of the International Union of Pure and Applied Chemistry. In an embodiment, the central metallic element is a Group 12 element.

The central metallic element may be at least one selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (Al), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb).

The organic ligand may include a functional group that is linkable to at least two metallic ions.

The hybrid porous material may have a single type of crystal morphology or single type of particle morphology. For example, the hybrid porous material may have a single crystal structure in the form of a hexahedron in which mesoporous silica is contained in an MOF structure.

However, the structure of the hybrid porous material is not limited to the structure illustrated in FIG. 1, and the hybrid porous material may also have various other crystal structures or crystal morphologies.

The hybrid porous material 10 may adsorb, store, and/or decompose different gases such as a volatile organic compound ("VOC") or carbon dioxide.

Hereinafter, an embodiment of a method of preparing the hybrid porous material will be described in further detail.

In an embodiment, the method of preparing the hybrid porous materials may include chemically bonding at least a first porous material and a second porous material. Herein, the term "chemically bonding" at least a first and a second porous material includes preparing at least one porous material (type I), and then impregnating the prepared at least one porous material (type I) with at least one of the precursor compounds (i.e., a raw materials) of at least one other type of porous material (type II), which is a different type of material than the at least one type of material (type I), and then reacting the impregnated at least one type of porous material (type I) with a remainder of the precursor compounds (i.e., raw materials) of the at least one other type of porous material (type II).

In an embodiment, the method of preparing the hybrid porous material may include impregnating a second porous material with a metal precursor or an organic ligand precursor for forming a first porous material that is a different material type than the second porous material; and reacting the impregnated second porous material with the organic ligand precursor or the metal precursor for forming the first porous material. For example, if the second porous material is impregnated with the metal precursor for forming the first porous material, the impregnated second porous material is then reacted with the organic ligand precursor for forming the first porous material. Alternatively, if the second porous material is impregnated with the organic ligand precursor for forming the first porous material, the impregnated second porous material is then reacted with the metal precursor for forming the first porous material.

The first porous material may include at least one material selected from the group consisting of an MOF compound, a ZIF compound, and derivatives thereof.

The second porous material may include at least one material selected from the group consisting of a porous silica (e.g. mesoporous silica), a porous alumina, a porous carbon, a zeolite, an activated carbon, a porous metal oxide, a porous clay, and an aerogel.

The metal precursor may include at least one metallic element selected from the group consisting of elements of the Periodic Table. For example, the metallic element may be at least one element selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (Al), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb).

The metal precursor may include, for example, at least one compound selected from the group consisting of a metal nitrate, a metal chloride, a metal bromide, a metal iodide, a metal acetate, a metal carbonate, a metal formate, a metal molybdate, a metal sulfate, a metal sulfide, a metal oxide, a metal fluoride, a metal phosphate, a metal perchlorate, a metal borate, and a metal hydroxide.

The organic ligand precursor may include an organic compound that is linkable to at least two metal elements, in particular metallic ions. The organic ligand precursor may include, for example, at least one organic compound selected from the group consisting of terephthalic acid, substituted terephthalic acid, tribenzoic acid, imidazole, substituted imidazole, pyridine, substituted pyridine, pyrazole, substituted pyrazole, tetrazole, and substituted tetrazole. In the present specification, the term "substituted" refers to a compound or radical where a hydrogen atom of the compound or radical is substituted with at least one (e.g., 1, 2, 3, 4, 5, 6 or more) substituents independently selected from a halogen group (i.e., F, Cl, Br, or I), a hydroxyl group, an alkyl group, an alkoxy group, an amine group, or a combination thereof, provided that the substituted atom's normal valence is not exceeded.

Hereinafter, an example of the method of preparing the hybrid porous material will be disclosed in further detail.

First, a metal precursor for forming a first porous material is dissolved in a first solvent to prepare a metal precursor solution. Separately, a second porous material that is a different type of material than the first porous material is prepared.

Then, the second porous material is sufficiently impregnated with the metal precursor solution and then dried to form a dried metal-containing second porous material.

Then, a ligand precursor for forming the first porous material is dissolved in the first solvent to prepare a ligand precursor solution.

Then, the dried metal-containing second porous material is added to the ligand precursor solution for forming the first porous material to form a mixture, and then the mixture is reacted, e.g., by heating the mixture to synthesize a hybrid porous material.

Finally, the synthesized hybrid porous material is washed with the first solvent, and then the first solvent is substituted with a second solvent that has a lower boiling point than the first solvent and is miscible with the first solvent. Then, the resulting product is dried to obtain a dried hybrid porous material.

One or more embodiments will be disclosed in further detail with reference to the following examples. These examples are for illustrative purposes only and are not intended to limit the scope of the disclosed embodiments.

EXAMPLES

Example 1

Synthesis of a Hybrid Porous Material

A 0.56 gram (g) quantity of $Zn(NO_3)_2 \cdot 4H_2O$ was dissolved in 3.2 milliliters (mL) of diethylformamide ("DEF") to prepare a metal precursor solution. Then, 0.8 g of mesoporous silica (Claytec, Inc., MSU-H) was added to the metal precursor solution to impregnate the mesoporous silica with the metal precursor solution. Then, impregnated mesoporous silica was dried at a temperature of 80° C. Then, 0.12 g of terephthalic acid was dissolved in 12 mL of DEF to prepare an organic ligand precursor solution. Then, the dried zinc-containing impregnated mesoporous silica was added to the organic ligand precursor solution, which had been heated at a temperature of 100° C., and then the mixture was maintained for one day at a temperature of 100° C., thereby forming a solid product. Then, the solid product was washed three times with DEF and then immersed in chloroform for three days to substitute DEF with chloroform. In this regard, in order to sufficiently perform the solvent substitution, the chloroform used was replaced with new chloroform in every 12 hours. Then, the resulting solid product was removed from the chloroform and dried at a temperature of 80° C., thereby obtaining a solvent-free hybrid porous material.

Comparative Example 1

Synthesis of a Porous Material

A solvent-free porous material was prepared in the same manner as in Example 1, except that 0.12 g of terephthalic acid and 0.56 g of $Zn(NO_3)_2 \cdot 4H_2O$ were dissolved in 12 mL of DEF to prepare a mixed solution including a metal precursor and a ligand precursor, and then 0.8 g of mesoporous silica (Claytec, Inc., MSU-H) was added to the mixed solution and the mixed solution heated to a temperature of 100° C. The mixed solution was maintained at a temperature of 100° C. (that is, the mesoporous silica was not impregnated with the metal precursor solution before the heating).

Comparative Example 2

Synthesis of an MOF Compound

A 0.12 g quantity of terephthalic acid and 0.56 g of $Zn(NO_3)_2 \cdot 4H_2O$ were dissolved in 12 mL of DEF to prepare a mixed solution including a metal precursor and a ligand precursor. Then, the mixed solution was heated at a temperature of 100° C. for 24 hours to prepare a solid product having a hexahedral structure (e.g. hexahedral particle morphology), and then the solid product formed on the wall of a reaction container was collected and washed three times with DEF and immersed in chloroform for 3 days so as to substitute DEF with chloroform. In this regard, in order to sufficiently perform the solvent substitution, the chloroform used was replaced with new chloroform in every 12 hours. Then, the resulting solid product was removed from the chloroform and then dried at a temperature of 80° C., thereby obtaining a solvent-free porous material.

Comparative Example 3

Preparation of Mesoporous Silica

Mesoporous silica (Claytec, Inc., MSU-H) was used for comparison with the properties of the hybrid porous material prepared according to Example 1.

Analysis Example

A scanning electron microscope ("SEM") image, energy dispersive spectroscopy ("EDX") spectrum, powder X-ray diffraction ("PXRD") spectrum, adsorption/desorption graph, and specific surface area and pore size of the hybrid porous material prepared according to Example 1 are respectively illustrated in FIGS. 2 through 4, and 6 and in Table 1 below.

Figure 5:
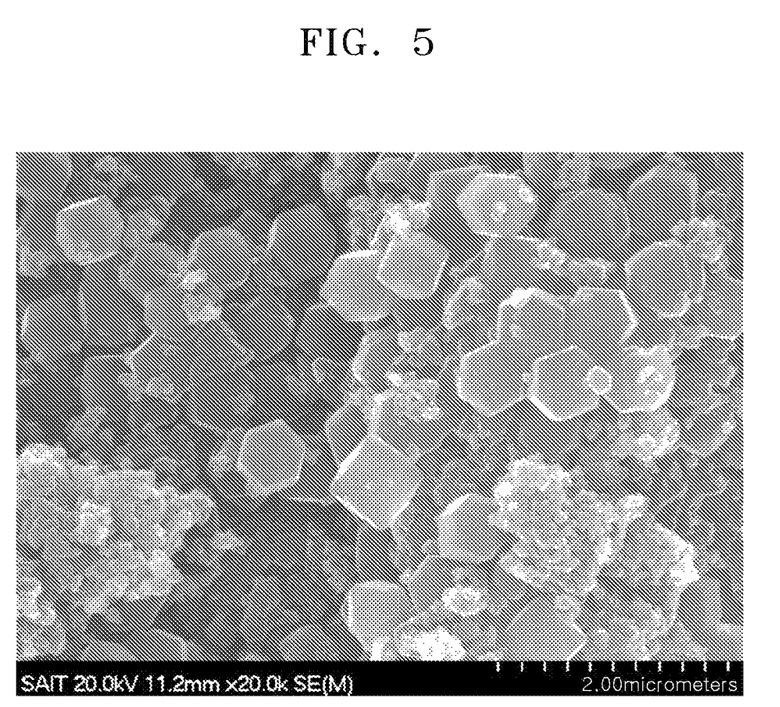
FIG. 5 is a SEM image of a porous material prepared according to Comparative Example 2.

A SEM image of the porous material prepared according to Comparative Example 1 is illustrated in FIG. 5.

A PXRD spectrum, adsorption/desorption graph, and specific surface area and pore size of the porous material prepared according to Comparative Example 2 are respectively illustrated in FIGS. 4 and 6 and Table 1 below.

In addition, an adsorption/desorption graph and specific surface area and pore size of the mesoporous silica of Comparative Example 3 are respectively illustrated in FIG. 6 and Table 1 below.

The SEM images, the EDX spectra, the PXRD spectra, adsorption/desorption graphs, and the specific surface area and pore size results were obtained as follows.

SEM Image Analysis

SEM image analysis was performed using S-4700 FE-SEM manufactured by Hitachi. The analysis sample was thin-film-coated with Pt before the analysis. The image magnification was 60 times and an accelerating voltage of 20 kilovolts (kV) was used.

EDX Spectrum Analysis

EDX spectrum analysis was performed using an EDX apparatus attached to S-4700 manufactured by Hitachi.

PXRD Spectrum Analysis

MP-XRD Xpert Pro equipment manufactured by Philips was used to obtain a PXRD spectrum, and a measurement angle was in the range of 5° to 30°. Each of the porous materials was milled and the obtained porous material powder was used as an analysis sample. The analysis was performed for the analysis sample while being wet with a solvent.

Adsorption/Desorption Graph Analysis

The adsorption/desorption graph was obtained by using a Tristar instrument manufactured by Micrometrics Inc. an adsorption temperature of 77 K. The analysis was performed using nitrogen gas. Before the analysis, each of the analysis samples was dried for 24 hours in a vacuum while being heated at a temperature of 110° C.

Specific Surface Area Analysis

Specific surface area was evaluated from the adsorption/desorption graphs by using Tristar 3000 version 6.05 software manufactured by Micrometrics Inc.

Pore Size Analysis

Pore size was evaluated from the adsorption/desorption graphs by using Tristar 3000 version 6.05 software manufactured by Micrometrics Inc.

TABLE 1

|  | Example 1 | Comparative Example 2 | Comparative Example 3 |
| --- | --- | --- | --- |
| Specific surface area ($m^2/g$) | 1,273 | 2,817 | 406 |
| Pore size (nm) | 2 to 7 | 2 to 3 | 6 to 7 |

Figure 2:
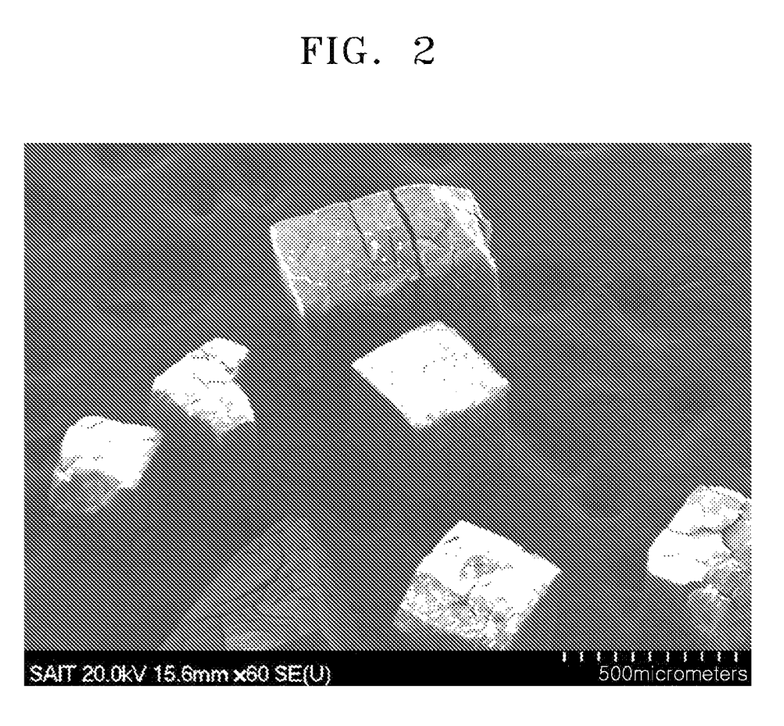
FIG. 2 is a scanning electron microscope ("SEM") image of a hybrid porous material prepared according to Example 1.
Figure 3:
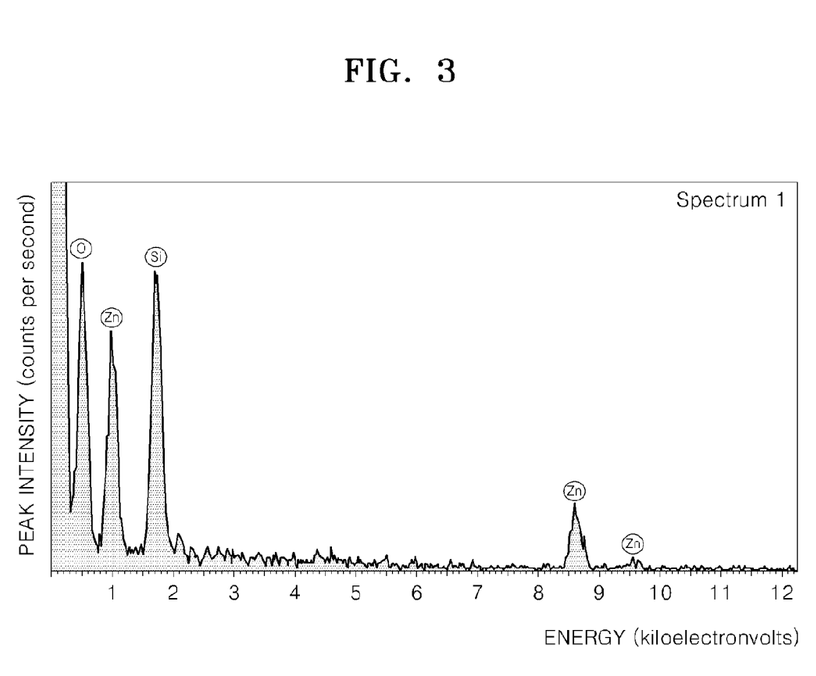
FIG. 3 is a graph of peak intensity (counts per second) versus energy (electron volts, eV) and is an energy dispersive spectroscopy ("EDX") spectrum of a hybrid porous material prepared according to Example 1.
Figure 4:
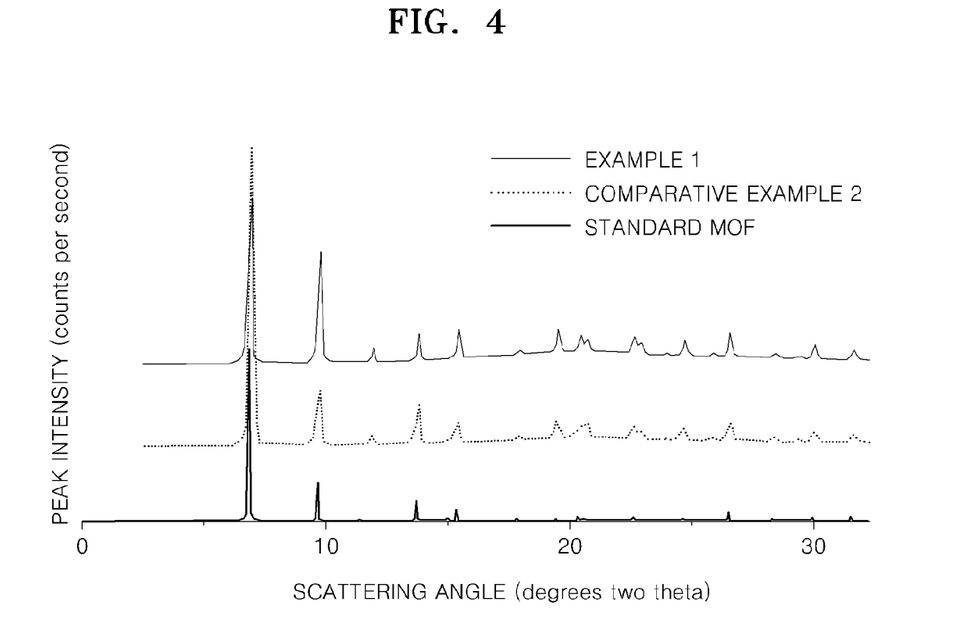
FIG. 4 is a graph of peak intensity (counts per second) versus diffraction angle (degrees two theta, 2θ) and shows X-ray diffraction ("XRD") spectra of a hybrid porous material prepared according to Example 1, a porous material prepared according to Comparative Example 2, and a standard metal-organic framework ("MOF") compound.
Figure 6:
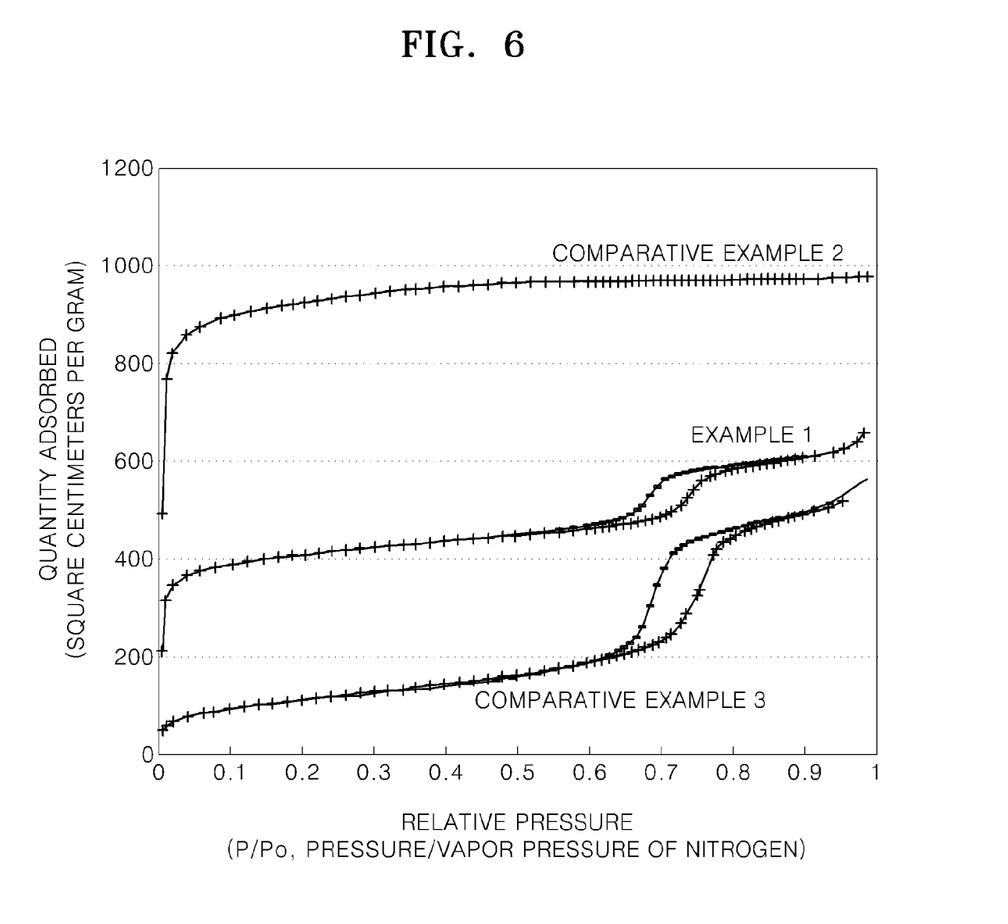
FIG. 6 is a graph of the quantity adsorbed (square centimeters per gram, $cm^2/g$) versus relative pressure (pressure/vapor pressure of nitrogen, P/Po) and shows adsorption and desorption of nitrogen by a hybrid porous material prepared according to Example 1, a porous material prepared according to Comparative Example 2, and mesoporous silica of Comparative Example 3.

FIGS. 2 and 3 are a scanning electron microscope ("SEM") image and an energy dispersive spectroscopy ("EDX") spectrum of the hybrid porous material prepared according to Example 1, respectively, FIG. 4 shows X-ray diffraction ("XRD") spectra of the hybrid porous material prepared according to Example 1, the porous material prepared according to Comparative Example 2, and the standard metal-organic framework ("MOF") compound, FIG. 5 is a SEM image of the porous material prepared according to Comparative Example 2, and FIG. 6 shows adsorption/desorption graphs of the hybrid porous material prepared according to Example 1, the porous material prepared according to Comparative Example 2, and mesoporous silica of Comparative Example 3.

The PXRD spectrum of the standard MOF compound illustrated in FIG. 4 was obtained as follows. The PXRD pattern was obtained from a crystal analysis result file of MOF-5 provided in Cambridge Crystal Structure Database, by using Diamond version 3.2c manufactured by Crystal Impact GbR. In this regard, an X-ray wavelength of 1.5406 Å and a measurement angle range of 5° to 30° were used as operating parameters of Diamond version 3.2c of Crystal Impact GbR.

Referring to FIGS. 2 through 4, and 6, the porous material prepared according to Example 1 has a hexahedral crystal structure (refer to FIG. 2), includes silicon and zinc (refer to FIG. 3), has the same PXRD spectrum as that of the standard MOF compound (refer to FIG. 4), and has characteristics of the MOF compound prepared according to Comparative Example 2 and characteristics of the mesoporous silica of Comparative Example 3 (refer to FIG. 6). In this regard, the porous material prepared according to Example 1 and the MOF compound according to Comparative Example 2 both have a steep slope at a relatively low relative pressure $P/P_0$ (pressure/vapor pressure of nitrogen) in the adsorption/desorption graph, and the porous material prepared according to Example 1 and the mesoporous silica of Comparative Example 3 both exhibit hysteresis in the adsorption/desorption graph (i.e., there is a portion of the adsorption/desorption graph in which the adsorption graph and the desorption graph do not match each other. In addition, it can be identified that the porous material prepared according to Comparative Example 2 is a MOF compound by matching of the PXRD spectrum of the porous material according to Comparative Example 2 with the PXRD spectrum of the standard MOF as shown in the PXRD spectra of FIG. 4.

Referring to FIGS. 2 and 3, it can be seen that the porous material prepared according to Example 1 is a hybrid compound, not a mixture. In addition, referring to Table 1, the specific surface area of the porous material prepared according to Example 1 is smaller than that of the MOF compound prepared according to Comparative Example 2, and greater than that of the mesoporous silica of Comparative Example 3. Also, the pore size of the porous material prepared according to Example 1 covers the pore size range of the MOF compound prepared according to Comparative Example 2 and the pore size range of the mesoporous silica of Comparative Example 3.

By taking into consideration all the analysis results disclosed above, it can be seen that the porous material prepared according to Example 1 is a hybrid porous material in which the MOF compound and the mesoporous silica are chemically bonded to each other.

In addition, referring to FIG. 5, phase separation occurred in the porous material prepared according to Comparative Example 1, which means that the porous material according to Comparative Example 1 is not a compound, but a mixture in which two types of materials were physically mixed, that is, a mixture in which the MOF compound and the mesoporous silica were physically mixed. Thus, it can be assumed that the mixed porous material would have the disadvantages of a MOF compound (that is, low stability with respect to humidity), and disadvantages of the mesoporous silica (that is, low adsorption capacity and difficult surface-modification).

It should be understood that the exemplary embodiments described therein should be considered in a descriptive sense only and not for purposes of limitation. Descriptions of features or aspects within each embodiment should be considered as available for other similar features or aspects in other embodiments.

What is claimed is:

1. A hybrid porous material comprising:
at least a first porous material portion and a second porous material portion, which are chemically bonded to each other and which are each a different type of material,
wherein each of the at least first and second porous material portions comprises at least one porous material selected from the group consisting of a metal-organic framework compound, a zeolitic imidazolate framework compound, and derivatives thereof, provided that the first porous material portion is not the same as the second porous material portion, and
wherein each of the metal-organic framework compound, the zeolitic imidazolate framework compound, and derivatives thereof comprises at least one central metallic element selected from the group consisting of metallic elements of elements of the Periodic Table, and an organic ligand.

2. The hybrid porous material of claim 1, wherein the central metallic element is at least one selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (Al), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb).

3. The hybrid porous material of claim 1, wherein the organic ligand comprises a functional group linkable to at least two metallic ions.

4. The hybrid porous material of claim 1, wherein the at least first and second porous material portions of the hybrid porous material comprise the metal-organic framework compound and the mesoporous silica which are chemically bonded to each other.

5. A method of preparing a hybrid porous material comprising at least a first porous material portion and a second porous material portion, which are chemically bonded to each other and are each a different type of material, the method comprising:
chemically bonding at least a first porous material and a second porous material, each of which are a different type of material, to form the hybrid porous material by impregnating a second porous material with a metal precursor or organic ligand precursor for forming the first porous material that is different in material type from the second porous material, and reacting the impregnated second porous material with the organic ligand precursor or metal precursor for forming the first porous material,
wherein each of the at least first and second porous material portions comprises at least one porous material selected from the group consisting of a metal-organic framework compound, a zeolitic imidazolate framework compound, and derivatives thereof.

6. The method of claim 5, wherein the first porous material comprises at least one material selected from the group consisting of the metal-organic framework compound, the zeolitic imidazolate framework compound, and derivatives thereof.

7. The method of claim 5, wherein the second porous material comprises at least one material selected from the group consisting of the porous silica, the porous alumina, the porous carbon, the zeolite, the activated carbon, the porous metal oxide, the porous clay, and the aerogel.

8. The method of claim 5, wherein the metal precursor comprises at least one metallic element selected from the group consisting of metallic elements of the Periodic Table.

9. The method of claim 8, wherein the metallic element is at least one selected from the group consisting of zinc (Zn), cobalt (Co), cadmium (Cd), nickel (Ni), manganese (Mn), chromium (Cr), copper (Cu), lanthanum (La), iron (Fe), platinum (Pt), palladium (Pd), silver (Ag), gold (Au), rhodium (Rh), iridium (Ir), ruthenium (Ru), lead (Pb), tin (Sn), aluminum (Al), titanium (Ti), molybdenum (Mo), tungsten (W), vanadium (V), niobium (Nb), tantalum (Ta), scandium (Sc), yttrium (Y), gallium (Ga), germanium (Ge), indium (In), bismuth (Bi), selenium (Se), and antimony (Sb).

10. The method of claim 5, wherein the metal precursor comprises at least one compound selected from the group consisting of a metal nitrate, a metal chloride, a metal bromide, a metal iodide, a metal acetate, a metal carbonate, a metal formate, a metal molybdate, a metal sulfate, a metal sulfide, a metal oxide, a metal fluoride, a metal phosphate, a metal perchlorate, a metal borate, and a metal hydroxide.

11. The method of claim 5, wherein the organic ligand precursor comprises an organic compound having a functional group linkable to at least two metallic ions.

12. The method of claim 11, wherein the organic ligand precursor comprises at least one organic compound selected from the group consisting of terephthalic acid, a substituted terephthalic acid, tribenzoic acid, imidazole, substituted imidazole, pyridine, a substituted pyridine, pyrazole, a substituted pyrazole, tetrazole, and a substituted tetrazole.

* * * * *